(12) United States Patent
Schmidt et al.

(10) Patent No.: US 7,297,378 B2
(45) Date of Patent: Nov. 20, 2007

(54) FLUORINATED FUSED AROMATICS AND THEIR USE IN LIQUID-CRYSTAL MIXTURES

(75) Inventors: Wolfgang Schmidt, Dreieich (DE); Rainer Wingen, Hofheim (DE); Barbara Hornung, Hasselroth (DE)

(73) Assignee: Merck Patent GmbH, Darmstadt (DE)

( * ) Notice: Subject to any disclaimer, the term of this patent is extended or adjusted under 35 U.S.C. 154(b) by 130 days.

(21) Appl. No.: 11/114,656

(22) Filed: Apr. 26, 2005

(65) Prior Publication Data

US 2005/0258397 A1 Nov. 24, 2005

(30) Foreign Application Priority Data

Apr. 26, 2004 (DE) ............ 10 2004 020 479

(51) Int. Cl.
*C09K 19/32* (2006.01)
*C07C 23/40* (2006.01)

(52) U.S. Cl. ............ 428/1.1; 252/299.62; 570/183; 570/187

(58) Field of Classification Search ............ 428/1.1; 252/299.62; 570/183, 187
See application file for complete search history.

(56) References Cited

U.S. PATENT DOCUMENTS

| | | | |
|---|---|---|---|
| 5,648,021 A | 7/1997 | Wingen et al. | |
| 5,888,422 A | 3/1999 | Manero et al. | |
| 6,168,838 B1 | 1/2001 | Schmidt et al. | |
| 6,558,758 B1 | 5/2003 | Yanai et al. | |
| 7,018,685 B2* | 3/2006 | Schmidt et al. | 428/1.1 |
| 7,067,179 B1* | 6/2006 | Ogawa et al. | 428/1.1 |
| 7,087,272 B2* | 8/2006 | Bremer et al. | 428/1.1 |
| 2004/0106798 A1 | 6/2004 | Bremer et al. | |
| 2004/0124399 A1 | 7/2004 | Schmidt et al. | |

FOREIGN PATENT DOCUMENTS

| | | |
|---|---|---|
| DE | 195 00 768 | 9/1995 |
| DE | 100 50 071 A1 | 6/2001 |
| EP | 0 837 851 | 4/1998 |
| EP | 0 946 473 | 10/1999 |
| EP | 1 201 632 A1 | 5/2002 |
| EP | 1 223 210 | 7/2002 |
| JP | 10-236992 | 9/1998 |
| WO | WO 01/10803 A1 | 2/2001 |
| WO | WO 02/055463 A1 | 7/2002 |
| WO | WO 02/079344 A1 | 10/2002 |

OTHER PUBLICATIONS

Ichinose et al., "High Optical Anisotropy and Small Rotational Viscosity LC Mixture for Field-Sequential Color TN-LCDs", IDW, LCT4-3, pp. 77-pp. 80 (2000).
Brown et al., "Aromatic Polyfluoro-Compounds_XXVIII1,2,3,4-Tetrafluorodibenzofuran and Some Nucleophilic Replacement Reactions", Tetrahedron, vol. 3, pp. 4041-pp. 4045 (1967).
Machine English Translation of JP 10-236992 from Japanese Patent office.
English langugae abstract of EP 1 223 210.

* cited by examiner

*Primary Examiner*—Shean C Wu
(74) *Attorney, Agent, or Firm*—Millen, White, Zelano & Branigan, P.C.

(57) ABSTRACT

Compounds of the formula (I)

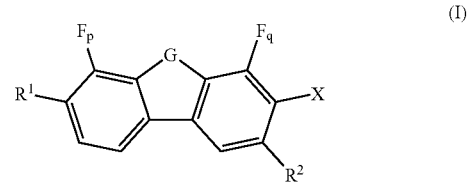

Figure 1:
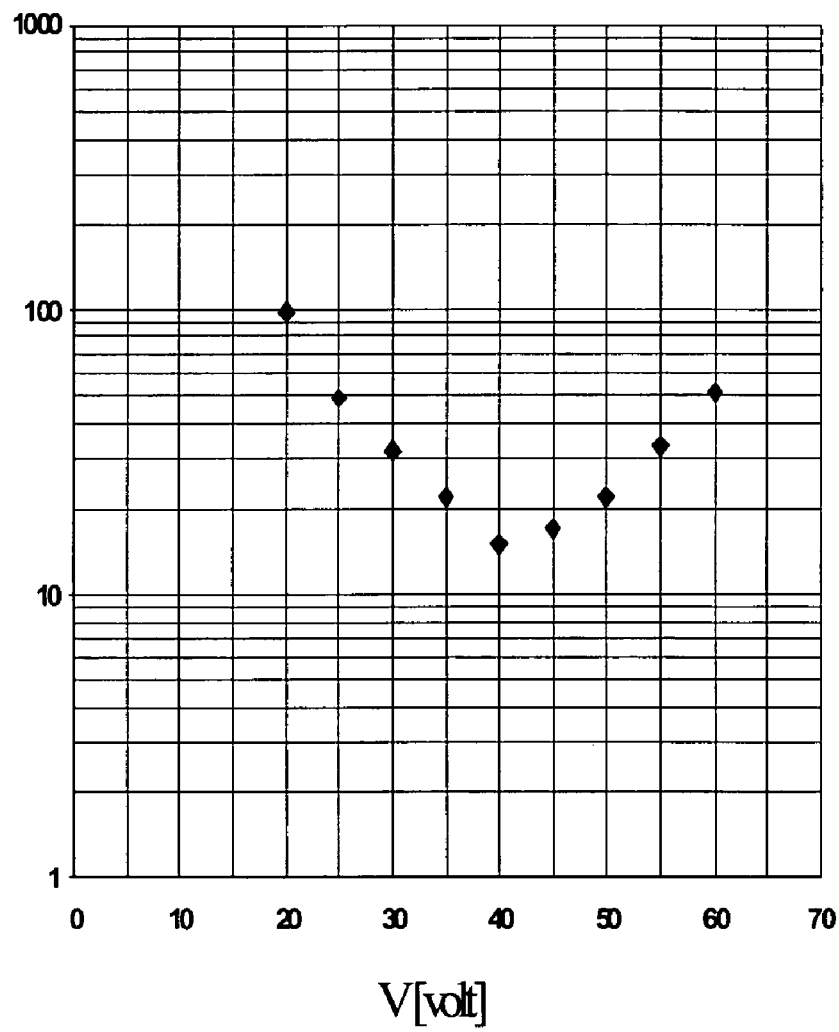

in which $R^1$, $R^2$, p, q, G and X are each as defined in the description,
  use of compounds of the formula (I) in liquid-crystal mixtures,
  liquid-crystal mixture comprising one or more compounds of the formula (I), and a
  liquid-crystal display comprising an inventive liquid-crystal mixture.

20 Claims, 1 Drawing Sheet

τ-Vmin curve (T$_C$ -30 K; monopolar pulse; 1.3 μm)

Response time τ [μs]

FLUORINATED FUSED AROMATICS AND THEIR USE IN LIQUID-CRYSTAL MIXTURES

This application claims priority to German Patent Application No. 10 2004 020 479.9, filed Apr. 26, 2004.

An ever-increasing number of applications of LCDs, for example for use in automobiles, in which a temperature range of from −40° C. to 100° C. can quite possibly exist, but also portable units such as cellphones and notebook PCs, requires liquid-crystal mixtures which have firstly a very wide working temperature range and secondly a very low threshold voltage.

There is therefore a continuing demand for novel, suitable liquid-crystal mixtures and mixture components. As described in Ichinose et al. (IDW'00, Abstr. LCT4-3) or in DE-A 100 50 071, materials are being sought in which there is coexistence of high optical anisotropy (Δn) and low rotational viscosity, although other parameters, for example high absolute values of dielectric anisotropy (Δε), are likewise preferentially required, in addition to further parameters relevant to the application.

1- and/or 8-fluorinated fluorenes having substituents in the 2 and 7 positions are known as components of liquid-crystal mixtures from WO 02/079344, WO 02/055463 and WO 01/010803.

Since the manufacturers of liquid-crystal displays, though, have a constant interest in improved liquid-crystal mixtures, there is still a need for further components of liquid-crystal mixtures, with which individual parameters relevant to the application, for example the dielectric anisotropy (Δε) or the optical anisotropy (Δn), may be optimized.

It is therefore an object of the present invention to provide novel components for use in nematic or cholesteric or chiral-smectic liquid-crystal mixtures which have high absolute values of dielectric anisotropy combined with a favorable ratio of viscosity to clearing point. In addition, the compounds should to a high degree preferably be light- and UV-stable, and also thermally stable. In addition, they should preferably be suitable for realizing a high voltage holding ratio (VHR). In addition, they should preferably have good synthetic accessibility and therefore potentially be inexpensive.

The objects are achieved in accordance with the invention by compounds of the formula (I)

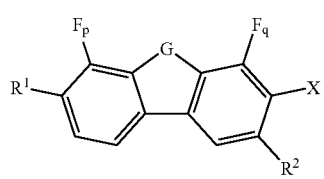

(I)

where:
$R^1$, $R^2$ are each independently
a) H
b) a straight-chain or branched alkyl radical having from 1 to 16 carbon atoms or a straight-chain or branched alkenyl radical having from 2 to 16 carbon atoms, in which
  b1) one or more nonadjacent and nonterminal $CH_2$ groups may be replaced by —O—, —C(=O)O—, —O—C(=O)—, —O—C(=O)—O—, —C(=O)— or —Si$(CH_3)_2$— and/or
  b2) one $CH_2$ group may be replaced by —C≡C—, cyclopropane-1,2-diyl, cyclobutane-1,3-diyl, cyclohexane-1,4-diyl or phenylene-1,4-diyl and/or
  b3) one or more hydrogen atoms may be replaced by F and/or Cl
c) -$M^1$-$A^1$-$R^5$ p, q are each independently 0 or 1, i.e., when the value is zero, —H is present at the appropriate position instead of —F $M^1$ is —CO—O—, —O—CO—, —CH$_2$—O—, —O—CH$_2$—, —CF$_2$—O—, —O—CF$_2$—, —CH=CH—, —CF=CF—, —C≡C—, —CH$_2$—CH$_2$—CO—O—, —O—CO—CH$_2$—CH$_2$—, —CH$_2$—CH$_2$—, —CF$_2$—CF$_2$—, —(CH$_2$)$_4$—, —OC(=O)CF=CF— or a single bond $A^1$ is 1,4-phenylene in which one or two hydrogen atoms may be replaced by F, Cl, CN and/or OCF$_3$ or three hydrogen atoms may be replaced by fluorine, 1,4-cyclohexylene in which one or two hydrogen atoms may be replaced by CH$_3$ and/or F, 1-cyclohexene-1,4-diyl in which one hydrogen atom may be replaced by CH$_3$ or F, pyrimidine-2,5-diyl, pyridine-2,5-diyl or 1,3-dioxane-2,5-diyl $R^5$ has the same possible definitions as specified for $R^1$ and $R^2$ with the exception of -$M^1$-$A^1$-$R^5$, but independently of the definition of $R^1$ and $R^2$ G is CH$_2$, C=O or CF$_2$ X is H, F, OCF$_3$, CF$_3$, OCF$_2$H, with the provisos that
a) at least one of p, q has to be 1
b) $R^1$ and $R^2$ must not at the same time be H
c) $R^2$ and X must not at the same time be H and by liquid-crystal mixtures comprising these compounds.

Preference is given to compounds of the formulae (Ia) to (Ie)

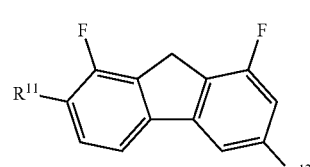

(Ia)

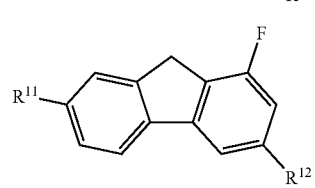

(Ib)

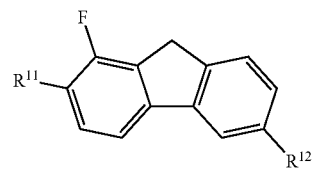

(Ic)

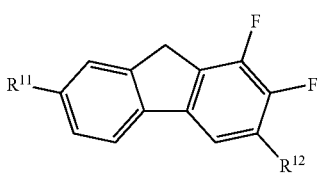

(Id)

-continued

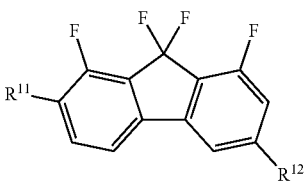
(Ie)

in which:

$R^{11}$ and $R^{12}$ are each independently an alkyl or alkyloxy radical having from 1 to 10 carbon atoms or an alkenyl or alkenyloxy radical having from 2 to 10 carbon atoms, in each of which one or more hydrogen atoms may also be replaced by F, or the $R^{15}\text{-}A^{15}\text{-}M^{15}$-moiety, with the proviso that:

$R^{11}$ and $R^{12}$ must not at the same time be $R^{15}\text{-}A^{15}\text{-}M^{15}$ $R^{15}$ is an alkyl or alkyloxy radical having from 1 to 10 carbon atoms or an alkenyl or alkenyloxy radical having from 2 to 10 carbon atoms $A^{15}$ is phenylene-1,4-diyl, cyclohexane-1,4-diyl $M^{15}$ is a single bond, —CO—O—, —O—CO—, —C≡C—, —OCF$_2$—, —CF$_2$O—, —CF$_2$CF$_2$—, —CH$_2$CH$_2$—.

Particular preference, especially for use in nematic mixtures, is given to the compounds of the formulae (Ia1), (Ia2), (Ie1) or (Ie2)

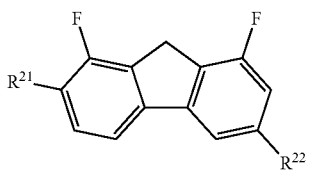
(Ia1)

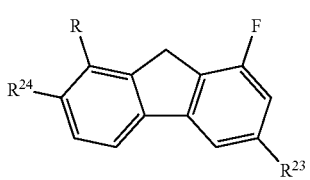
(Ia2)

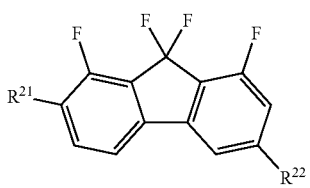
(Ie1)

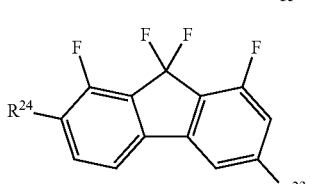
(Ie2)

in which:

$R^{21}$ and $R^{22}$ are each independently an alkyl or alkyloxy radical having from 1 to 6 carbon atoms or an alkenyl or alkenyloxy radical having from 2 to 5 carbon atoms, $R^{23}$ is an alkyl or alkyloxy radical having from 1 to 6 carbon atoms or an alkenyl or alkenyloxy radical having from 2 to 5 carbon atoms, $R^{24}$ is the $R^{15}\text{-}A^{15}\text{-}M^{15}$- moiety in which $R^{15}$ is an alkyl or alkyloxy radical having from 1 to 10 carbon atoms or an alkenyl or alkenyloxy radical having from 2 to 10 carbon atoms $A^{15}$ is phenylene-1,4-diyl, cyclohexane-1,4-diyl $M^{15}$ is a single bond or —CH$_2$CH$_2$—.

The provision of compounds of the formula (I) in a quite general sense considerably broadens the range of liquid-crystalline substances which are suitable for producing liquid-crystalline mixtures from different performance aspects.

In this context, the compounds of the formula (I) have a broad field of application. Depending on the selection of the substituents, they may be added to other classes of compound, in order, for example, to influence the dielectric and/or optical anisotropy of such a dielectric. They may also serve to optimize its threshold voltage and/or its viscosity. The compounds may also serve to increase the mesophase range or to adjust individual mesophases to parameters relevant to the application.

The compounds of the formula (I) are particularly suitable, even in small amounts in the mixture, for influencing the dielectric anisotropy (Δε) and/or the optical anisotropy Δn of liquid-crystal mixtures. The compounds of the formula (I) are particularly suitable, even in small amounts in the mixture, for reducing the response time of ferroelectric liquid-crystal mixtures. The compounds of the formula (I) are likewise particularly suitable for adjusting the broadness of the $S_C$ or N phase to application requirements.

The present invention thus provides compounds of the formula (I) and for the use of these compounds as components of liquid-crystalline mixtures and liquid-crystalline mixtures comprising one or more compounds of the formula (I).

The compounds of the formula (I) may be used in various liquid-crystal mixtures, for example chiral-smectic, nematic or cholesteric liquid-crystal mixtures. In the case of nematic mixtures, they are particularly suitable for active matrix displays (AM-LCD) (see, for example, C. Prince, Seminar Lecture Notes, Volume I, p. M-3/3-M-22, SID International Symposium 1997, B. B. Bahadur, Liquid Crystal Applications and Uses, Vol. 1, p. 410, World Scientific Publishing, 1990, E. Lüder, Recent Progress of AMLCD's, Proceedings of the 15$^{th}$ International Display Research Conference, 1995, p. 9-12) and in-plane-switching displays (IPS-LCD), and, in the case of smectic liquid-crystal mixtures, for smectic (ferroelectric or antiferroelectric) displays. Further display possibilities are the ECB and VA display mode in the case of nematic and cholesteric LC mixtures.

Further components of liquid-crystal mixtures which comprise inventive compounds of the formula (I) are preferably selected from the known compounds having smectic and/or nematic and/or cholesteric phases. Mixture components suitable in this context are listed in particular in WO 00/36054, DE-A-195 31 165 and EP-A-0 893 424, which are explicitly incorporated herein by way of reference.

The present invention therefore also provides liquid-crystal mixtures, which comprise at least one compound of the formula (I), preferably in an amount of from 1 to 40% by weight, based on the liquid-crystal mixture. The mixtures preferably comprise at least 3 further components of smectic and/or nematic and/or cholesteric phases in addition to compounds of the formula (I). The invention additionally provides electrooptical display elements (liquid-crystal displays) which comprise the inventive mixtures.

Preference is given to displays which comprise the inventive nematic or smectic (ferroelectric or antiferroelectric) mixtures in combination with active matrix elements.

The inventive displays are typically constructed in such a way that one liquid-crystal layer is enclosed on both sides by layers which are typically, in this sequence starting from the LC layer, at least one alignment layer, electrodes and a boundary layer (for example of glass). In addition, they may comprise spacers, adhesive frames, polarizers and thin color filter layers for color displays. Further possible components are antireflection, passivation, compensation and barrier layers, and also electrically nonlinear elements such as thin-film transistors (TFT) and metal-insulator-metal (MIM) elements. The construction of liquid-crystal displays has already been described in detail in relevant monographs (see, for example, E. Kaneko, "Liquid Crystal TV Displays: Principles and Applications of Liquid Crystal Displays", KTK Scientific Publishers, 1987).

Examples of possible synthetic routes to compounds of the formula (I) are specified in the schemes which follow, although other processes are also feasible and possible.

The following abbreviations are used:
n-BuLi n-butyllithium
s-BuLi sec-butyllithium
DME dimethoxyethane
DMF N,N-dimethylformamide
DMSO dimethyl sulfoxide
KOtBu potassium tert-butoxide
LDA lithium diisopropylamide
LICKOR n-butyllithium+potassium tert-butoxide
LITMP lithium 2,2,6,6-tetramethylpiperidide
MEK methyl ethyl ketone (2-butanone)
MTBE tert-butyl methyl ether
PCC pyridinium chlorochromate
THF tetrahydrofuran
4-TsOH 4-toluenesulfonic acid

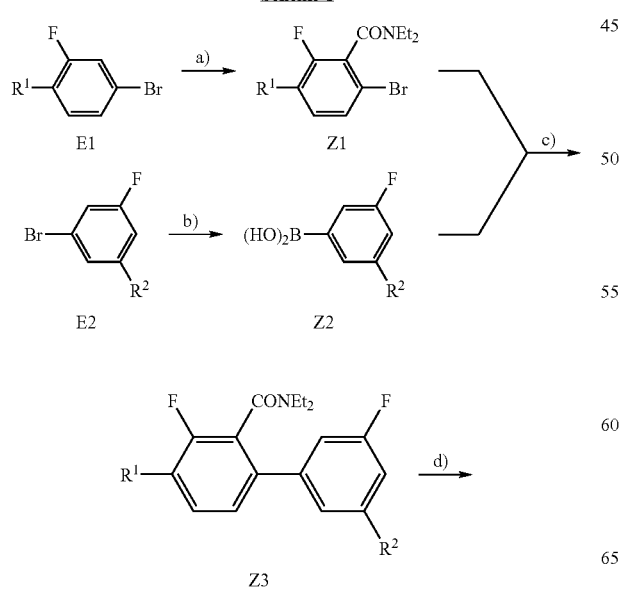

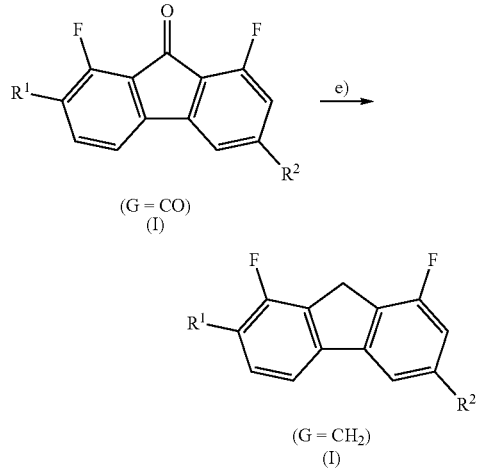

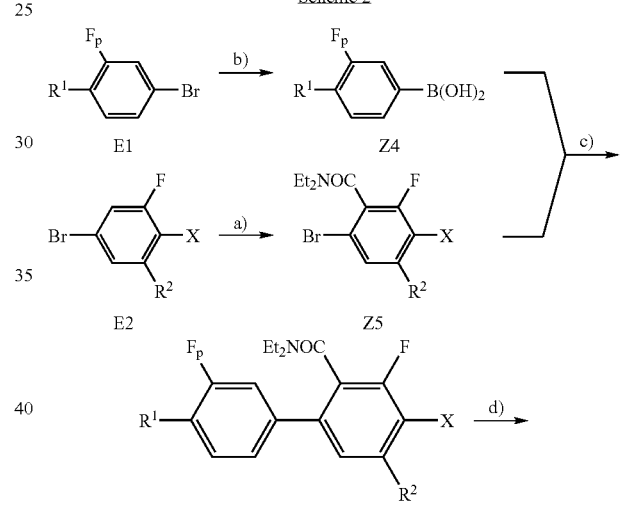

a) 1. LDA or LITMP 2. $CO_2$ 3. $H_3O^+$ according to *Tetrahedron Lett.* 1996, 37, 6551 4. $SOCl_2$ 5. $Et_2NH$ according to *Organikum, VEB Deutscher Verlag der Wissenschaften,*

15 th Ed., Berlin, 1984, Ch. 7.1.5, pp. 529 and 513; *Bull. Korean Chem. Soc.* 1993, 14, 732 b) 1. Mg 2. B(OMe)$_3$ 3. H$_3$O$^+$ according to *Mol. Cryst. Liq. Cryst.* 1991, 195, 221; WO 00/04111 c) Pd-Katalysator according to *J. Org. Chem.* 1991, 56, 1683; *Synthesis* 1998, 1195; *Can. J. Chem.* 2000, 78, 905-919; *J. Chem. Soc., Perkin Trans.* 2 1999, 481; *J. Chem. Soc., Perkin Trans.* 2, 2000, 27; *J. Am. Chem. Soc.* 2000, 122, 4020; *Tetrahedron Lett.* 2001, 42, 6523 d) LDA/THF according to *J. Org. Chem.* 1991, 56, 1683; *Synthesis* 1998, 1195 e) Et$_3$SiH/CF$_3$COOH according to *J. Org. Chem.* 1973, 38, 2675; *Mol. Cryst. Liq. Cryst.* 1991, 199, 327

Some reactants E1 where R$^1$=alkyl or R$^1$=alkyloxy (Scheme 1) and p=1 (Scheme 2) are known from the literature and can be prepared, for example, from commercially available 1-bromo-3-fluoro-4-iodobenzene [105931-73-5] or from commercially available 4-bromo-2-fluorophenol [2105-94-4] according to the procedure described in WO 00/0411 and Mol. Cryst Liq. Cryst. 1991, 195, 221. Reactants E1 where p=0 (Scheme 2) are familiar to those skilled in the art (for example J. Chem. Soc., Perkin Trans. 2, 1989, 2041) and some are even commercially available.

The reactant E2 where R$^2$=methyl is known from the literature [202865-83-6] and commercially available. Reactants E2 where R$^2$=alkyl can be prepared from the compound E2 where R$^2$=CHO [188813-02-7] which is known from the literature by Wittig reaction with alkyltriphenylphosphonium halides and subsequent hydrogenation; alternatively, the commercially available compound where R$^2$=CN [179898-34-1] may be reacted with alkylmagnesium halides and subsequently processed reductively to the target compounds. Reactants E2 where R$^2$=OMe [29578-39-0] and OEt [212307-87-4] are known from the literature; higher homologs may be obtained, for example, from 3-bromo-5-fluorophenol (E2 where R$^2$=OH) [433939-27-6] may be obtained by Williamson etherification with alkyl bromides. The reactant E2 where R$^2$=H and X=F [348-61-8] (Scheme 2) is commercially available.

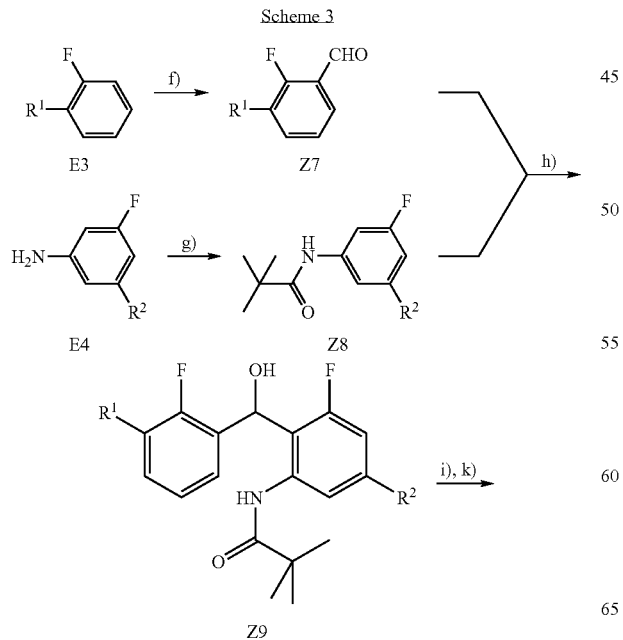

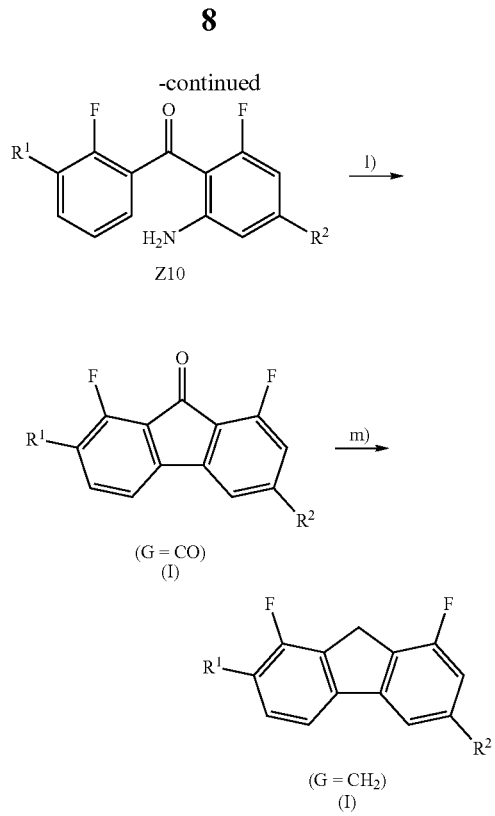

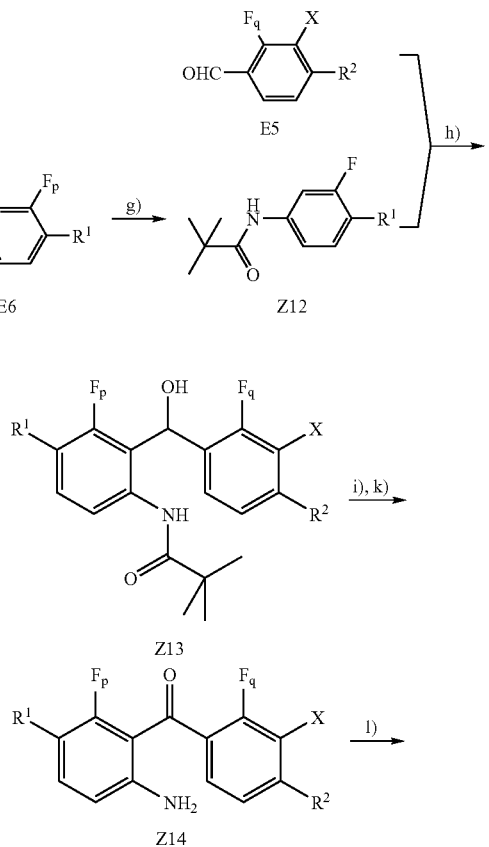

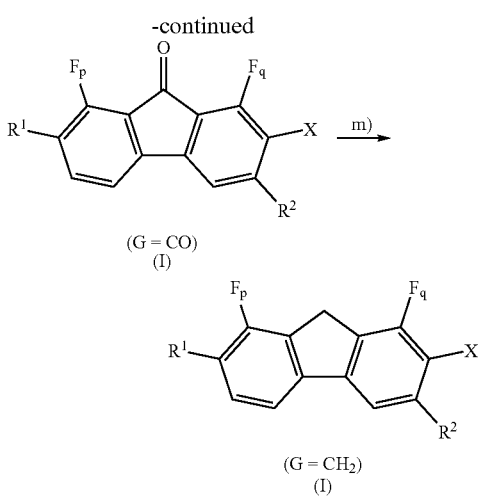

(G = CO)
(I)

(G = CH₂)
(I)

f) 1. LICKOR 2. DMF 3. H₃O⁺ according to *Synlett* 1991, 119; *Synth. Commun.* 1990, 20, 1701; GB 1,098,387; EP 1 153 909
g) Pivaloyl chloride/CHCl₃/pyridine according to *J. Chin. Chem. Soc* 1991, 38, 41
h) n-BuLi/THF according to *J. Chin. Chem. Soc* 1991, 38, 41
i) PCC/CH₂Cl₂ according to *J. Chin. Chem. Soc* 1991, 38, 41
k) 1. H₂SO₄ 2. NaOH according to *J. Chin. Chem. Soc* 1991, 38, 41
l) 1. Isoamyl nitrite 2. HBF₄/MeOH 3. Δ according to *J. Chin. Chem. Soc* 1991, 38, 41
m) Et₃SiH/CF₃COOH according to *J. Org. Chem.* 1973, 38, 2675; *Mol. Cryst. Liq. Cryst.* 1991, 199, 327

Reactants E3 where R¹=alkyl, 4-alkylcyclohexyl can be obtained, for example, from commercially available 1-bromo-2-fluorobenzene [1072-85-1] (E3 where R¹=Br) by metalation with n-BuLi and subsequent, successive reaction with appropriate aldehydes or cyclohexanones, dehydration with phosphorus pentoxide and hydrogenation (according to J. Chem. Soc., Perkin Trans II 1989, 2041; ibid. 1999, 481) or directly from fluorobenzene according to Recl. Trav. Chim. Pays-Bas 1994, 113, 529. Reactants E3 where R¹=alkyloxy can be obtained from commercially available 2-fluorophenol [367-12-4] (E3 where R¹=OH) by Williamson etherification with alkyl bromides.

The reactant E4 where R²=methyl [52215-41-5] is known from the literature. Higher homologs where R²=alkyl can be prepared, for example, from 1-bromo-3-fluoro-5-nitrobenzene [10472-88-5] (prepared from commercially available 4-fluoro-2-nitroaniline [364-78-3] by bromination and subsequent deamination) or commercially available 1-fluoro-3-iodo-5-nitrobenzene [3819-88-3] by reaction with alkynes (according to J. Org. Chem. 1998, 63, 8551; Tetrahedron Lett. 1975, 4467) and subsequent hydrogenation or reduction. The reactant E4 where R²=methoxy [2339-58-4] is known from the literature (for example Bull. Soc. Chim. 1937, 5, 1636); higher homologs where R²=alkyloxy can be obtained analogously.

Reactants E5 where q=0 and X=H (Scheme 4) are commercially available (for example 4-methoxybenzaldehyde [123-11-5], 4-ethylbenzaldehyde [4748-78-1], 4-n-propyloxybenzaldehyde [5736-85-6], 4-n-pentylbenzaldehyde [6853-57-2]). Reactants E5 where q=1 and X=H can be prepared by metalating the corresponding 4-alkyl-1-bromo-2-fluorobenzenes or 4-alkyloxy-1-bromo-2-fluorobenzenes with n-BuLi and subsequently reacting with DMF according to GB 1,098,387 or EP 1 153 909. Some of the 4-alkyloxy-1-bromo-2-fluorobenzenes and 4-alkyl-1-bromo-2-fluorobenzenes are described in the literature and are obtainable, for example, starting from 4-bromo-3-fluorophenol [121219-03-2] by Williamson etherification with alkyl bromides, or starting from commercially available 1-bromo-2-fluoro-4-iodobenzene [136434-77-0] analogously to the procedure described in WO 00/0411, Mol. Cryst Liq. Cryst. 1991, 195, 221 and ibid. 1991, 204, 43. The reactant 2,3-difluorobenzaldehyde [2646-91-5] (E5 where q=1, X=F and R²=H) is commercially available; homologs where R²=alkyl or alkyloxy can be prepared from 1-alkyl-2,3-difluorobenzenes or 1-alkyloxy-2,3-difluoro-benzenes known to those skilled in the art (for example J. Chem. Soc., Perkin Trans. 2, 1989, 2041) analogously to the procedure described in GB 1,098,387.

Reactants E6 where p=0 are commercially available (for example 4-ethylaniline [589-16-2], 4-n-propylaniline [2696-84-6], 4-n-butylaniline [104-13-2], 4-methoxyaniline [104-94-9]). 3-Fluoro-4-methoxyaniline [366-99-4] (E6 where p=1 and R¹=methoxy) is commercially available; higher homologs where R¹=alkyloxy can be obtained from commercially available 2-fluoro-4-nitrophenol [403-19-0] by Williamson etherification with alkyl bromides and subsequent reduction of the nitro group (according to J. Med. Chem. 2000, 43, 4701; U.S. Pat. No. 4,431,807). 3-Fluoro-4-methylaniline [452-77-7] (E6 where p=1 and R¹=methyl) is commercially available; higher homologs where R¹=alkyl can be prepared, for example, from 2-fluoro-1-iodo-4-nitrobenzene [2996-30-7] (J. Org. Chem. 1960, 25, 996) by reacting with alkynes (according to J. Org. Chem. 1998, 63, 8551; Tetrahedron Lett. 1975, 4467) and subsequently hydrogenating or reducing, or from 2-fluoro-4-nitrobenzaldehyde [157701-72-9] by Wittig reaction with alkyltriphenyl-phosphonium halides and subsequent hydrogenation or reduction.

Compounds of the formula (I) where G=CH₂, q=1, X=F and R²=H (Schemes 2 and 4) can be converted, after metalation with LICKOR, by reaction with alkyl bromides (according to Recl. Trav. Chim. Pays-Bas 1994, 113, 529; Synth. Commun. 1990, 20, 1701), to corresponding inventive compounds (I) where R²=alkyl. Alternatively, corresponding inventive compounds where R²=alkyloxy can be prepared by metalating with n-BuLi or s-BuLi, reaction with trimethyl borate, acid hydrolysis and oxidation with hydrogen peroxide (according to J. Chem. Soc., Perkin Trans. 2, 1989, 2041; ibid. 1999, 481).

Compounds (Ie) can be synthesized in analogy to the synthesis of 9,9-difluorofluorenes starting from fluoren-9-ones, as described, for example, in J. Org. Chem. 1981, 46, 3917; J. Chem. Soc., Chem. Commun. 1995, 177; Synlett 1991, 191; Tetrahedron 1996, 52, 9 and WO 02/079344.

The invention is illustrated in detail by the examples below.

EXAMPLE 1

2-Butyloxy-1,8-difluoro-6-propylfluoren-9-one

Compound (I) Where G=CO, p=q=1, X=H,
R¹=OC₄H₉, R²=C₃H₇

Under protective gas, 18.5 g of 3-fluoro-5-propylphenyl-boronic acid [prepared from 1,3-dibromo-5-fluorobenzene by lithiation with n-BuLi and subsequent reaction with DMF (U.S. Pat. No. 6,391,907), Wittig reaction of the resulting 3-bromo-5-fluorobenzaldehyde with ethyltriphenylphosphonium bromide (according to US 2003 0229096), hydrogenation of the resulting 1-bromo-3-fluoro-5-propenylbenzene with platinum oxide in ethanol and final reaction with magnesium and trimethyl borate (according to J. Chem. Soc., Perkin Trans. II 1989, 2041)], 17.7 g of anhydrous potassium fluoride and 1.27 g of tris(dibenzylideneacetone)dipalladium(0) are initially charged and admixed successively with a solution of 31.9 g of N,N-diethyl-6-bromo-3-butyloxy-2-fluorobenzamide [prepared from 4-bromo-2-fluorophenol by Williamson etherification with 1-bromobutane and potassium carbonate in acetone, subsequent lithiation with LITMP in THF at −70° C. and reaction with carbon dioxide (according to Tetrahedron Lett. 1996, 37, 6551), conversion of the resulting 6-bromo-3-butyloxy-2-fluorobenzoic acid to the corresponding acid chloride with thionyl chloride and reaction with diethylamine] in 175 ml of dry 1,4-dioxane and 0.84 g of tri-tert-butylphosphine (dissolved in approx. 10 ml of the same solvent). The mixture is heated to boiling with vigorous stirring for 8 h. After cooling, the reaction mixture is added to water and extracted repeatedly with MTBE. The combined org. phases are washed with sat. sodium chloride solution and dried over sodium sulfate, and the solvents are removed under reduced pressure. The crude product is purified by chromatography on silica gel with heptane/ethyl acetate (8:2 v/v) as eluent and recrystallization from heptane. The 4-butyloxy-3,3'-difluoro-5'-propylbiphenyl-2-carboxylic acid diethylamide obtained is dissolved in 120 ml dry THF and added dropwise to a solution of LDA in 60 ml THF, cooled to −30° C. (obtained from 14 ml diisopropylamine and 65 ml n-Buli (1.6 M solution in hexane)). Stirring is continued for 3 h and subsequently quenching is performed using saturated ammonium chloride solution. The reaction mixture is brought to 0° C. and acidified with HCl. After extracting with MTBE the combined organic phases are washed with 5% sodium hydrogen carbonate solution and saturated NaCl solution and dried with sodiumsulfate. After removing the solvent in vacuo the residue is purified by chromatography on silica gel with heptane/ethyl acetate (95:5 v/v) as eluent and twofold recrystallization from heptane. 5.1 g of 2-butyloxy-1,8-difluoro-6-propylfluoren-9-one are obtained.

EXAMPLE 2

2-Butyloxy-1,8-difluoro-6-propylfluorene

Compound (I) Where G=CH$_2$, p=q=1, X=H, R$^1$=OC$_4$H$_9$, R$^2$=C$_3$H$_7$

Under exclusion of moisture, 3.8 g of 2-butyloxy-1,8-difluoro-6-propylfluoren-9-one (example 1) are dissolved in 50 ml of trifluoroacetic acid, and 4.6 ml of triethylsilane are added dropwise slowly at a temperature of 5-20° C. with gentle cooling. The mixture is subsequently stirred at room temperature for 1 h and then at 40-70° C. for 4 h. After cooling, the reaction mixture is added to water and extracted with dichloromethane. The combined org. phases are washed with water and 5% sodium hydrogencarbonate solution and dried over sodium sulfate. After the solvent has been removed in vacuo, the yellow residue is purified chromatographically on silica gel using 8:2 heptane/dichloromethane as eluent. After the solvent had been removed in vacuo, the product-containing fractions were recrystallized from heptane. 1.2 g of 2-butyloxy-1,8-difluoro-6-propylfluorene were obtained.

EXAMPLE 3

1,8-Difluoro-2,6-di-n-propylfluoren-9-one

Compound (I) Where G=CO, p=q=1, X=H, R$^1$=R$^2$=C$_3$H$_7$

Analogously to example 1, using N,N-diethyl-6-bromo-2-fluoro-3-propyl-benzamide [prepared from 4-bromo-2-fluoro-1-propylbenzene by lithiation with LITMP in THF at −70° C., reaction with carbon dioxide (according to Tetrahedron Lett. 1996, 37, 6551), conversion of the resulting 6-bromo-2-fluoro-3-propylbenzoic acid to the corresponding acid chloride using thionyl chloride, and reaction with diethylamine; 4-bromo-2-fluoro-1-propylbenzene is obtained from 4-bromo-2-fluoro-1-iodobenzene and propyne according to WO 00/0411] instead of N,N-diethyl-6-bromo-3-butyloxy-2-fluorobenzamide, 1,8-difluoro-2,6-di-n-propylfluoren-9-one is obtained.

EXAMPLE 4

1,8-Difluoro-2,6-di-n-propylfluorene

Compound (I) Where G=CH$_2$, p=q=1, X=H, R$^1$=R$^2$=C$_3$H$_7$

Analogously to example 2, using 1,8-difluoro-2,6-di-n-propylfluoren-9-one instead of 2-butyloxy-1,8-difluoro-6-propylfluoren-9-one, 1,8-difluoro-2,6-di-n-propylfluorene is obtained.

USE EXAMPLE 1

A chiral-smectic C mixture consisting of 2-(4-Heptyloxyphenyl)-5-nonylpyrimidine 19.6%

5-Nonyl-2-(4-octyloxyphenyl)pyrimidine 19.6%

5-Nonyl-2-(4-nonyloxyphenyl)pyrimidine 19.6%

2-(2,3-Difluoro-4-heptyloxyphenyl)-5-nonylpyrimidine 6.5%

2-(2,3-Difluoro-4-octyloxyphenyl)-5-nonylpyrimidine 6.5%

2-(2,3-Difluoro-4-nonyloxyphenyl)-5-nonylpyrimidine 6.5%

5-Hexyloxy-2-(4-hexyloxyphenyl)pyrimidine 19.6%

(S)-4-[4'-(2-Fluorooctyloxy)biphenyl-4-yl]-1-heptyl cyclohexanecarbonitrile 2.0% is admixed with 5% of the compound from example 1. This results in a mixture which, as demonstrated by FIG. 1 is suitable for the operation of displays in inverse mode, since the curved profile has the required minimum and the values are within the technically relevant range.

FIG. 1 shows the τVmin curve (τ plotted against the voltage) at T$_C$-30K, monopolar pulses and a cell separation of 1.3 μm.

What is claimed is:

1. A compound of formula (I)

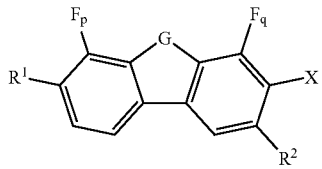

wherein
$R^1$ is
a) H
b) a straight-chain or branched alkyl radical having 1 to 16 carbon atoms or a straight-chain or branched alkenyl radical having 2 to 16 carbon atoms, in which
b1) one or more nonadjacent and nonterminal $CH_2$ groups may be replaced by —O—, —C(=O)O—, —O—C(=O)—, —O—C(=O)—O—, —C(=O)— or —Si(CH$_3$)$_2$—, and/or
b2) one $CH_2$ group may be replaced by —C≡C—, cyclopropane-1,2-diyl, cyclobutane-1,3-diyl, cyclohexane-1,4-diyl or phenylene-1,4-diyl and/or
b3) one or more hydrogen atoms may be replaced by F and/or Cl, or
c) -$M^1$-$A^1$-$R^5$, $R^2$ is
b) a straight-chain or branched alkyl radical having 1 to 16 carbon atoms or a straight-chain or branched alkenyl radical having 2 to 16 carbon atoms, in which
b1) one or more nonadjacent and nonterminal $CH_2$ groups may be replaced by —O—, —C(=O)O—, —O—C(=O)—, —O—C(=O)—O—, —C(=O)— or —Si(CH$_3$)$_2$—, and/or
b2) one $CH_2$ group may be replaced by —C≡C—, cyclopropane-1,2-diyl, cyclobutane-1,3-diyl, cyclohexane-1,4-diyl or phenylene-1,4-diyl and/or
b3) one or more hydrogen atoms may be replaced by F and/or Cl, or
c) -$M^1$-$A^1$-$R^5$ p, q are, each independently, 0 or 1, wherein at the value zero, —H is present at the appropriate position instead of —F $M^1$ is —CO—O—, —O—CO—, —CH$_2$—O—, —O—CH$_2$—, —CF$_2$—O—, —O—CF$_2$—, —CH=CH—, —CF=CF—, —C≡C—, —CH$_2$—CH$_2$—CO—O—, —O—CO—CH$_2$—CH$_2$—, —CH$_2$—CH$_2$—, —CF$_2$—CF$_2$—, —(CH$_2$)$_4$—, —OC(=O)CF=CF— or a single bond, $A^1$ is 1,4-phenylene in which one or two hydrogen atoms may be replaced by F, Cl, CN and/or OCF$_3$ or three hydrogen atoms may be replaced by fluorine, 1,4-cyclohexylene in which one or two hydrogen atoms may be replaced by CH$_3$ and/or F, 1-cyclohexene-1,4-diyl in which one hydrogen atom may be replaced by CH$_3$ or F, pyrimidine-2,5-diyl, pyridine-2,5-diyl or 1,3-dioxane-2,5-diyl, $R^5$ is
a) H
b) a straight-chain or branched alkyl radical having 1 to 16 carbon atoms or a straight-chain or branched alkenyl radical having 2 to 16 carbon atoms, in which
b1) one or more nonadjacent and nonterminal $CH_2$ groups may be replaced by —O—, —C(=O)O—, —O—C(=O)—, —O—C(=O)—O—, —C(=O)— or —Si(CH$_3$)$_2$—, and/or
b2) one $CH_2$ group may be replaced by —C≡C—, cyclopropane-1,2-diyl, cyclobutane-1,3-diyl, cyclohexane-1,4-diyl or phenylene-1,4-diyl and/or
b3) one or more hydrogen atoms may be replaced by F and/or Cl, G is CH$_2$, C=O or CF$_2$,
X is H, F, OCF$_3$, CF$_3$, or OCF$_2$H,
with the proviso that
at least one of p, q has to be 1.

2. A compound as claimed in claim 1, which is of formula (Ia1), (Ia2), (Ie1) or (Ie2)

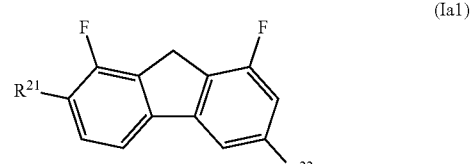

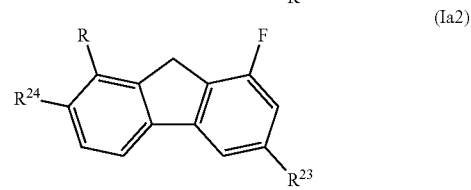

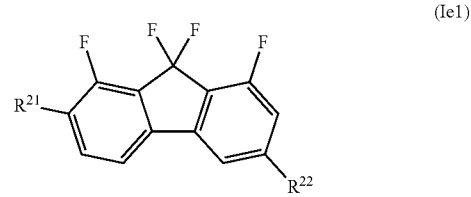

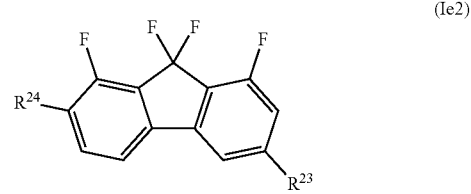

wherein:
$R^{21}$ and $R^{22}$ are each independently an alkyl or alkyloxy radical having 1 to 6 carbon atoms or an alkenyl or alkenyloxy radical having 2 to 5 carbon atoms,
$R^{23}$ is an alkyl or alkyloxy radical having 1 to 6 carbon atoms or an alkenyl or alkenyloxy radical having 2 to 5 carbon atoms,
$R^{24}$ is $R^{15}$-$A^{15}$-$M^{15}$-
$R^{15}$ is an alkyl or alkyloxy radical having 1 to 10 carbon atoms or an alkenyl or alkenyloxy radical having 2 to 10 carbon atoms,
$A^{15}$ is phenylene-1,4-diyl, or cyclohexane-1,4-diyl, and
$M^{15}$ is a single bond or —CH$_2$CH$_2$—.

3. A liquid-crystal mixture, comprising one or more compounds of the formula (I) as claimed in claim 1.

4. A liquid-crystal mixture as claimed in claim 3, which comprises one or more compounds of formula (I) in an amount of 1 to 40% by weight based on the liquid-crystal mixture.

5. A liquid-crystal mixture as claimed in claim 3, which comprises at least three further components of smectic and/or nematic and/or cholesteric phases.

6. A liquid-crystal mixture as claimed in claim 3, which is chiral-smectic.

7. A liquid-crystal mixture as claimed in claim 3, which is nematic or cholesteric.

8. A liquid-crystal display comprising a liquid-crystal mixture as claimed in claim 3.

9. A liquid-crystal display as claimed in claim 8, which is operated in ECB, IPS or VA display mode and comprises a nematic or cholesteric liquid-crystal mixture.

10. A liquid-crystal mixture, comprising one or more compounds of claim 2.

11. A liquid-crystal display comprising a liquid-crystal mixture as claimed in claim 10.

12. A compound as claimed in claim 1, which is of formula (Ia1), (Ia2), (Ie1) or (Ie2)

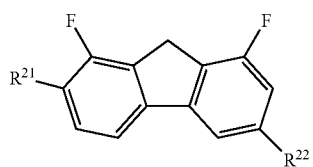
(Ia1)

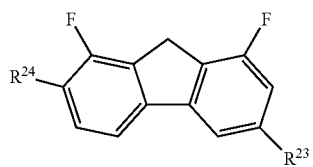
(Ia2)

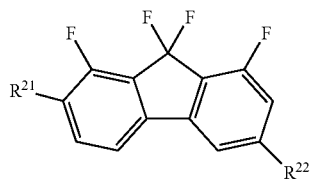
(Ic1)

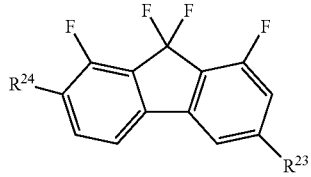
(Ie2)

wherein
$R^{21}$ and $R^{22}$ are, each independently, an alkyl or alkyloxy radical having 1 to 6 carbon atoms or an alkenyl or alkenyloxy radical having 2 to 5 carbon atoms, $R^{23}$ is an alkyl or alkyloxy radical having 1 to 6 carbon atoms or an alkenyl or alkenyloxy radical having 2 to 5 carbon atoms, $R^{24}$ is $R^{15}$-$A^{15}$-$M^{15}$-, $R^{15}$ is an alkyl or alkyloxy radical having 1 to 10 carbon atoms or an alkenyl or alkenyloxy radical having 2 to 10 carbon atoms, $A^{15}$ is phenylene-1,4-diyl, or cyclohexane-1,4-diyl, and
$M^{15}$ is a single bond or —$CH_2CH_2$—.

13. A liquid-crystal mixture, comprising one or more compounds of claim 12.

14. A liquid-crystal display comprising a liquid-crystal mixture as claimed in claim 13.

15. A compound as claimed in claim 1, which is 2-Butyloxy-1,8-difluoro-6-propylfluoren-9-one; 2-Butyloxy-1,8-difluoro-6-propylfluorene; 1,8-Difluoro-2,6-di-n-propylfluoren-9-one; or 1,8-Difluoro-2,6-di-n-propylfluorene.

16. A liquid-crystal mixture, comprising one or more compounds of claim 15.

17. A liquid-crystal display comprising a liquid-crystal mixture as claimed in claim 16.

18. A compound as claimed in claim 1, wherein $R^2$ is -$M^1$-$A^1$-$R^5$.

19. A liquid-crystal mixture, comprising one or more compounds of claim 18.

20. A liquid-crystal display comprising a liquid-crystal mixture as claimed in claim 19.

* * * * *